United States Patent
Amirav et al.

(10) Patent No.: US 10,497,548 B1
(45) Date of Patent: Dec. 3, 2019

(54) METHOD AND APPARATUS FOR ELECTRON IONIZATION LIQUID CHROMATOGRAPHY MASS SPECTROMETRY

(71) Applicant: Aviv Amirav, Hod Hasharon (IL)

(72) Inventors: Aviv Amirav, Hod Hasharon (IL); Alexander B. Fialkov, Tel Aviv (IL); Svetlana Tsizin, Holon (IL)

(73) Assignee: AVIV AMIRAV, Hod Hasharon (IL)

( * ) Notice: Subject to any disclaimer, the term of this patent is extended or adjusted under 35 U.S.C. 154(b) by 0 days.

(21) Appl. No.: 16/400,315

(22) Filed: May 1, 2019

(51) Int. Cl.
*H01J 49/00* (2006.01)
*G01N 30/72* (2006.01)

(52) U.S. Cl.
CPC ........ *H01J 49/0054* (2013.01); *G01N 30/724* (2013.01); *G01N 30/7206* (2013.01); *H01J 49/0031* (2013.01)

(58) Field of Classification Search
CPC .............. H01J 49/0054; H01J 49/0031; G01N 30/724; G01N 30/7206
See application file for complete search history.

(56) References Cited

U.S. PATENT DOCUMENTS

| | | | |
|---|---|---|---|
| 8,604,424 B2 | 12/2013 | Amirav | |
| 2010/0301209 A1* | 12/2010 | Ouyang | ......... H01J 49/0495 250/288 |
| 2013/0219991 A1* | 8/2013 | Ebeler | ................ G01N 30/7206 73/23.37 |
| 2016/0003787 A1* | 1/2016 | Wright | ............... G01N 30/7266 250/282 |
| 2016/0123936 A1* | 5/2016 | Chen | ..................... H01J 49/145 250/282 |

OTHER PUBLICATIONS

Cappiello, A. et al., "An Efficient Liquid Chromatography-Mass Spectrometry Interface for the Generation of Electron Ionization Spectra," Anal. Chem. 72, 3841-3846, (2000).

(Continued)

*Primary Examiner* — Nicole M Ippolito
*Assistant Examiner* — Sean M Luck
(74) *Attorney, Agent, or Firm* — Dann, Dorfman, Herrell and Skillman, P.C.

(57) ABSTRACT

In a method and apparatus for electron ionization liquid chromatography mass spectrometry (EI-LC-MS) analysis liquid chromatograph output solvent flow is directed together with spray formation gas into a spray formation and vaporization chamber for forming spray droplets which are vaporized to form vaporized sample compounds at a pressure equal to or greater than ambient pressure. A minor portion is conveyed into a heated flow restriction capillary that directly connects the spray formation and vaporization chamber and a non-fly-through electron ionization ion source of a mass spectrometer located inside a vacuum chamber. A major portion is released to atmosphere so that it does not enter the flow restriction capillary and therefore does not reach the non-fly-through electron ionization ion source. Also disclosed is an interface for a unified dual-mode mass spectrometer system for performing gas chromatography mass spectrometry (GC-MS) or electron ionization liquid chromatography mass spectrometry (EI-LC-MS) analyses.

34 Claims, 3 Drawing Sheets

(56) References Cited

OTHER PUBLICATIONS

Cappiello, A. et al., "Advanced Liquid Chromatography-Mass Spectrometry Interface Based on Electron Ionization," Anal. Chem. 79, 5364-5372, (2007).

Termopoli, V. et al., "Atmospheric Pressure Vaporization Mechanism for Coupling a Liquid Phase with Electron Ionization Mass Spectrometry," Anal. Chem.89, 2049-2056, (2017).

Seeman, B. et al., "Electron Ionization LC-MS with Supersonic Molecular Beams—The New Concept Benefits and Applications" J. Mass. Spectrom. 50, 1252-1263 (2015).

Amirav, A. et al., "Gas chromatography-mass spectrometry with supersonic molecular beams", J. Mass. Spectrom. 43, 141-163 (2008).

* cited by examiner

METHOD AND APPARATUS FOR ELECTRON IONIZATION LIQUID CHROMATOGRAPHY MASS SPECTROMETRY

FIELD OF THE INVENTION

The present invention relates to electron ionization liquid chromatography mass spectrometry.

BACKGROUND OF THE INVENTION

Liquid chromatography-mass spectrometry (LC-MS) has become an established, widely used analytical technique. Electrospray ionization (ESI) is by far the most popular LC-MS ionization method due to its high sensitivity, robustness and extended sample molecular weight range. ESI is sometimes supplemented and complemented with atmospheric pressure chemical ionization (APCI) and atmospheric pressure photo ionization (APPI) which in some cases show better performance with relatively small and less polar compounds. However, ESI, APCI and APPI still suffer from limitations in having poor or no ionization of non-polar compounds, are characterized by non-uniform compound-specific response and are plagued by ion suppression effects. In addition, all these atmospheric pressure ionization (API) methods are soft techniques that usually produce protonated molecular ions, hence requiring expensive high resolution accurate mass MS for analyte identification and characterization.

Consequently, electron ionization (EI) with its fragment-rich mass spectral pattern can significantly benefit LC-MS through the provision of automated library based identification with sample compound names and structures at the isomer level. In addition, EI seems ideally suitable for the LC-MS identification of unknown compounds that are not in the library, due to its provision of extensive fragment ions information. EI-LC-MS can also facilitate faster LC-MS analysis through the elimination of ion suppression effects that plague ESI and/or APCI and it is characterized by superior response uniformity for improved quantitation of unknown compounds.

Thus, combining EI with LC-MS is clearly highly valuable if the past problems of particle beam EI-LC-MS of limited sensitivity, poor linear dynamic range and limited range of compounds amenable for analysis can be solved.

Cappiello and co-workers developed a miniaturized version of Particle Beam EI-LC-MS [1] and later-on developed a new approach named Direct EI [2] that was demonstrated in a range of applications. This Direct EI interface was based on thermally assisted spray at the entrance of the EI ion source without any nebulizing gas. Recently they further improved their EI-LC-MS interface in their Liquid EI [3] in which the sample is thermally vaporized in its mass spectrometer transfer line that is connected with an electron ionization ion source. However, all the currently available EI-LC-MS are based on in-vacuum or reduced pressure thermally assisted spray formation from the LC output liquid flow. Consequently, they are limited to low, sub 1 µL/min LC liquid solution output flow rate and have no vaporized gas split line [2, 3]. Furthermore, the use of thermally assisted spray is known to exhibit liquid sample line clogging problems due to thermal condensation and/or decomposition of portion of the sample compounds and their matrices. In addition, service to the clogged liquid delivery capillary requires lengthy LC-MS system venting and pump down. As a result, these approaches suffer from limited concentration sensitivity, poor robustness and require tedious service.

Seemann et al. [4] and Amirav [5] developed and described another EI-LC-MS interface and system that is based on the transfer of vaporized sample compounds into a supersonic nozzle, expanding these vaporized sample compounds plus vaporized solvent and nebulizing helium gas from the supersonic nozzle into a differentially pumped vacuum chamber that is equipped typically with a 250 L/s turbo molecular pump, skimming the generated supersonic jet with a skimmer and generating a collision free supersonic molecular beam (SMB) of vibrationally cold sample molecules. These cold sample molecules in the SMB are collimated and pass axially inside a unique design of a fly-through electron ionization ion source that has zero internal electric field and the ionized sample compounds are further collimated and 90° deflected into the mass analyzer of a mass spectrometer for their mass spectrometery analysis. While EI-LC-MS with SMB is an effective EI-LC-MS method is it expensive, complex and difficult to be coupled with existing quadrupole MS such as of GC-MS with their available standard in vacuum EI ion sources. In addition, the electron ionization mass spectra of cold molecules in the SMB are characterized by enhanced molecular ions and thus are perceived as having lower matching factors with the EI mass spectra libraries.

Thus, there is still a clear need for a low cost EI-LC-MS system that can accept and analyze standard LC-MS flow rates, is reliable, robust, easy to use and service and that can be based on existing EI ion sources.

An important downside of EI-LC-MS that impedes its development despite its clear and well known benefits is that while APCI and/or APPI can be easily exchanged with ESI either automatically or via a minor and fast change of the LC-MS hardware without system venting, EI-LC-MS due to its in-vacuum ion source requires a separate mass spectrometer system, which is expensive.

Currently, analytical mass spectrometry is divided into mostly GC-MS or LC-MS and only in rare cases can one find a mass spectrometer system of LC-MS with APCI that can provide both GC-MS and LC-MS in a single MS system. Even in these cases, changing their mode of operation requires a change of hardware such as physical movement of the heavy and bulky GC towards the MS of the LC-MS plus some additional hardware changes in the APCI chamber. On the other hand, there is no GC-MS with EI and LC-MS with EI in a single MS system. Clearly having such universal chromatography MS system of both LC and GC coupled with a single MS is highly desirable and beneficial since it can save cost, valuable laboratory bench space and reduce system maintenance and manpower owing to the need to operate one system as opposed to two systems. Preferably, such a system should also enable the mode of operation to be changed under software requiring only a click (or few clicks) of the mouse without any hardware change.

BRIEF DESCRIPTION OF THE INVENTION

It is therefore an object of the present invention to provide a highly reliable robust and easy to service EI-LC-MS interface and an EI-LC-MS and GC-MS in one MS system with automated mode of operation change that does not require any change to the hardware.

This object is realized in accordance with the invention by a method and system having the features of the respective independent claims.

BRIEF DESCRIPTION OF THE DRAWINGS

The invention will now be described in connection with certain preferred embodiments with reference to the following illustrative figures, so that it may be more fully understood. With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of said claims.

In the drawings.

DETAILED DESCRIPTION OF THE INVENTION

In the following description of some embodiments, identical components that appear in more than one figure or that share similar functionality will be referenced by identical reference symbols.

Figure 1:
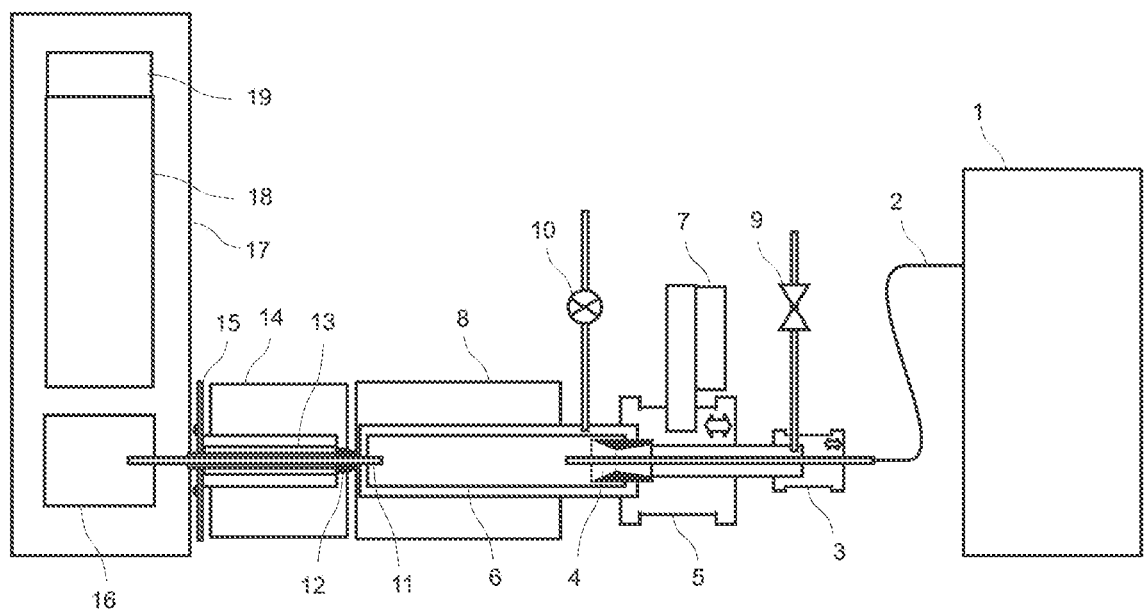
FIG. 1 is a schematic diagram illustrating the Electron Ionization LC-MS system according to an embodiment of the present invention.

Referring to FIG. 1 there is shown an electron ionization (EI) interface for combination with LC-MS to form an effective EI-LC-MS system. A principal feature of the interface is that it is based on pneumatic nebulization of the LC output liquid solvent flow at above ambient atmospheric pressure and the full thermal vaporization of the spray and sample compounds takes place at a spray formation and vaporization chamber at above ambient pressure. We note that if we have a split line connected to ambient pressure, the pressure inside the spray formation and vaporization chamber must be above ambient. Another central ingredient of our method and mass spectrometer system is the transfer of a portion of the vaporized sample molecules together with the nebulizing gas and solvent vapor into the in-vacuum EI ion source via a heated flow restriction capillary that transfers a small yet tunable portion of the vaporized solvent sample and nebulizing gas mixture into the mass spectrometer electron ionization ion source while the majority of this gas and vapor exits out of the system to the ambient environment via a heated split valve and typically into a solvent and waste container. The spray formation and vaporization chamber is further characterized by having a large thermal gradient at its entrance to prevent premature onset of thermospray and irregular liquid jumps and spray instabilities. An air cooling unit is therefore included to reduce the spray formation and vaporization chamber input temperature to well below the boiling point of the LC solvents.

The EI-LC-MS system includes a liquid chromatography (LC) component (1) into which a sample is introduced, its liquid solvent flow output being transferred via a tube (2) into the EI-LC-MS interface (items 3-15) through a liquid capillary axial longitudinal motion adjustment unit (3) that enables careful axial positioning of the end of the LC output liquid flow capillary at the pneumatic spray formation orifice (4). The EI-LC-MS interface further includes another axial longitudinal motion adjustment mechanism (5) of the pneumatic spray formation orifice (4) at the spray formation and vaporization chamber (6) at an optimal temperature zone that enables steady spray formation without bubble jumps and spray irregularities yet close enough to the zone that is sufficiently hot for the full sample vaporization from its dried spray particles with minimal or no LC peak tailing. To ensure the required large temperature gradient at the beginning of the spray formation and vaporization chamber (6) there is further provided an air cooling unit (7) based on a cooling air fan and an aluminum bar heat transfer unit or alternatively on a Peltier electronic cooler. Typical spray formation and vaporization chamber entrance temperature is below 50° C. and a typical temperature gradient at the beginning of the spray formation and vaporization chamber is above 200° C./cm in part via the use of GC glass liner with its low heat conductivity for the main body of the spray formation and vaporization chamber.

The spray formation and vaporization chamber is heated by a heater (8) and the spray formation orifice (4) is operated with added pneumatic spray gas, typically helium that is introduced via a valve (9) to improve the sensitivity although the use of nitrogen and/or other gases is also possible. The spray helium gas flow can be split via a flow splitter (not shown) so that about 10% of its flow will arrive outside the spray orifice to prevent sample back-migration at the outside of the spray orifice that can lead to peak tailing. The spray of the sample and LC solvent is induced by the nebulizing helium gas flow at the spray formation orifice (4) that is placed at the beginning of the spray formation and vaporization chamber. The spray formation and vaporization chamber is typically made of a deactivated GC injector glass liner that is heated at the 200-350° C. temperature range for full sample compounds vaporization from the spray formed particles. Helium is the most useful nebulizing gas since in any case it is available as the most widely used GC column carrier gas and it affects the least the performance of EI ion sources by space charge. Typical Helium nebulizing spray gas flow rate is 150 ml/min. Electrospray, ultrasound and thermally assisted spray can also be used but pneumatic spray seems the most robust, suitable and straightforward.

The full mixture of vaporized sample, solvent and gas flow is split via a heated split valve (10) and its majority exits to the ambient pressure environment, typically into a solvent and waste container while a small portion of this mixture is introduced into a capillary flow restrictor (11) that is sealed with a ferrule (12) at the above atmospheric pressure side of the spray formation and vaporization chamber. The capillary flow restrictor is placed in a transfer line (13) that is heated by an independent heating element (14) and that is sealed at the mass spectrometer vacuum side by a sealing flange (15). The capillary flow restrictor transfers the sample vapor and vaporized solvent and pneumatic spray gas into an EI ion source (16) that is placed inside a vacuum chamber (17) and the electron ionization produced ions are mass analyzed by a mass analyzer (18) that is typically a quadrupole mass analyzer (but can alternatively be a time of flight MS) and detected by ion detector (19). Typically the nebulizing helium gas flow rate is 136 ml/min, orifice external sheath gas flow rate is 14 ml/min and the heated flow restriction capillary flow rate is adjusted via its length and internal diameter to transfer about 1 ml/min gas and solvent vapor which is typically the equivalent solvent liquid flow rate of 0.3 µL/min so that at LC column flow rate of 50 µL/min we have a split ratio of 166. Typical flow restriction capillary is the same as used in GC transfer lines, namely a Vespel coated fused silica capillary with 0.35 mm O.D. and 0.1 mm I.D. at a typical length of 28 cm. The flow restriction capillary can transfer 1.0 ml/min helium at 300° C. transfer line temperature and 1.5 Bar absolute pressure. Note that the transferred sample solvent and gas amount can be tuned by the split valve closure or opening that controls the vaporization chamber pressure (quadratic pressure dependence).

While the above describes the use of in-vacuum electron ionization ion source, clearly one can similarly use an in-vacuum chemical ionization (CI) ion source instead of EI and thereby obtain CI-LC-MS with the benefit of enhanced protonated molecular ions. However, the use of a standard electron ionization ion source for LC-MS according to the present invention allows the user to obtain chemical ionization mass spectra with the same EI ion source without its replacement and without adding any CI reagent compound since the user can control and increase the solvent flow rate into the ion source and thereby obtain CI mass spectra with the solvent molecules such as methanol or water without any hardware change.

The method and mass spectrometer apparatus for electron ionization liquid chromatography mass spectrometry (EI-LC-MS) according to the present invention are characterized by several unique and highly desirable and even surprising benefits including:

A. The spray formation and vaporization chamber is operated at above ambient pressure and the flow restriction capillary protects the EI ion source and mass analyzer vacuum chamber from leaks when the vaporization chamber is open to the environment. Thus, the spray formation and vaporization chamber can be serviced via a simple and quick replacement of its liner without venting and without any worry of a major leak as the air flow into vacuum is limited to below a safe very low value of 0.5 ml/min.

B. Easy service further implies that non-volatile buffers can be used with periodic liner replacements hence resulting in improved LC-MS analyses.

C. The use of pneumatic spray instead of thermally assisted thermospray results in a major improvement of the EI interface robustness and stability. Thermally assisted spray inevitably results in frequent clogging of the liquid delivery capillary via solid matter deposition, the same as limestone deposit is formed in a domestic tea kettle. Thus, the use of pneumatic induced spray with liquid temperatures below their boiling points significantly reduces such clogging effects, and even if they do occur, which is rare, service is easy and quick.

D. In order to further improve the pneumatic spray we employ a large axial temperature gradient at the spray formation and vaporization chamber liner to suppress the possibility of formation of solvent bubbles that can result in irregular spray. The temperature gradient can be higher than 60° C./cm at the liner entrance.

E. The full LC column output liquid flow rate up to 250 µL/min is passed into the spray formation and vaporization chamber and the vast majority thereof is split out after its vaporization. This practice is far superior to the alternative of splitting the vast majority of liquid flow before its spray formation since handling sub µL/min liquid flow rate is difficult and subject to various hard-to-detect liquid leaks, dead volumes effects and change of the liquid flow rate due to onset of tiny liquid transfer line clogging while accurate control of the vaporized solvent and spray gas is much easier and more accurate. Accordingly, our method allows the use of standard LC columns with internal diameters of 1 or 2 mm with liquid flow rates above 20 µL/min (up to 250 µL/min) which is well above the sub 1 µL/min used in nano LC columns.

F. In order to optimize the pneumatic spray stability and directionality the spray source can include a spray head in which the liquid delivery capillary is placed within 0.3 mm upstream of the pneumatic spray generation orifice up to 1 mm downstream of the orifice with the aid of a positioning device. In addition, the pneumatic spray is performed with a spray head positioning device that can place it in the spray formation and vaporization chamber at a selected temperature zone that is cool enough to eliminate onset of thermospray instabilities yet close enough to a hot zone of the spray vaporization chamber to provide tailing free sample full vaporization. Consequently, we can obtain with the pneumatic spray source as above a highly directional fine spray that contacts the heated surface of the spray formation and vaporization liner at a hot surface.

G. The heated flow restriction capillary aims at vaporized liquid flow rate reduction into the electron ionization ion source below 1 µL/min and typically at 0.3 µL/min equivalent liquid flow rate. Since the capillary length is typically fixed by the structure e.g. to 28 cm, the flow rate into the EI ion source is adjusted by the internal diameter of the fused silica capillary ($D^4$ dependence, where D is diameter) and head pressure at the spray formation and vaporization chamber which can be controlled via the split valve adjustment ($P^2$ dependence, where P is pressure). This is an important benefit of the invention over hitherto-proposed EI-LC-MS methods and it allows the user to optimize the sensitivity, suppress onset of chemical ionization and largely improve the EI ion source filament lifetime.

H. The use of spray formation and vaporization chamber with a liner means that if sample and or matrix decomposition occurs, it contaminates the spray formation and vaporization liner, which is easy to service and replace and not the metallic surface of the EI ion source that is difficult to service and requires venting and lengthy and delicate cleaning.

I. The typical position of the spray formation and vaporization chamber is at the entrance of a modified GC-MS transfer line although a few other locations can be considered.

Seemann et al. [4] and Amirav [5] describe a unique electron ionization LC-MS with a supersonic molecular beam interface and contact-free fly-through EI ion source. While their interface shares some components with the above-described interface in that it provides a pneumatic assisted spray at above ambient pressure, there is no suggestion to provide an EI-LC-MS with a standard i.e. non-fly-through electron ion source that has a closed metallic ionization chamber with electric field gradient. The use of supersonic molecular beams significantly complicates the apparatus and increases its price and thus deters from using it. In addition, contrary to our approach the flow restriction capillary of Seemann et al. [4] and Amirav [5] leads to a supersonic nozzle and not directly into an in-vacuum EI ion source. Most importantly is the fact that with the use of supersonic expansion with its added differential pumping vacuum chamber most of the LC output liquid flow is directed into the supersonic nozzle with minimal or no splitting into the environment. In sharp contrast, according to the present invention the LC output liquid undergoes after vaporization major splitting with typical split ratio of over 100, the split ratio being adjusted to optimize the sensitivity and filament lifetime as well as suppressing the onset of intra-ion-source chemical ionization. The success of our approach with about 100 times lower flow rate than Seemann et al. and Amirav is surprising since in order to protect the EI ion source we need to use a flow restriction capillary with 100 times higher flow restriction thus with the much narrower fused silica capillary with 100 μm internal diameters. Such narrow capillaries are highly susceptible to clogging (partial and/or full) and the 100 times higher split ratio inevitably results in a much lower signal that could be considered as unattractive. Accordingly, Seemann et al. and Amirav teaches away from the invention whose success is highly surprising yet attractive in view of the simplicity of the MS system.

The present invention also discloses a combined unified EI-LC-MS and GC-MS system with a single shared mass spectrometer ion source and mass analyzer that is characterized by automated mode of operation change without any hardware change.

Figure 2:
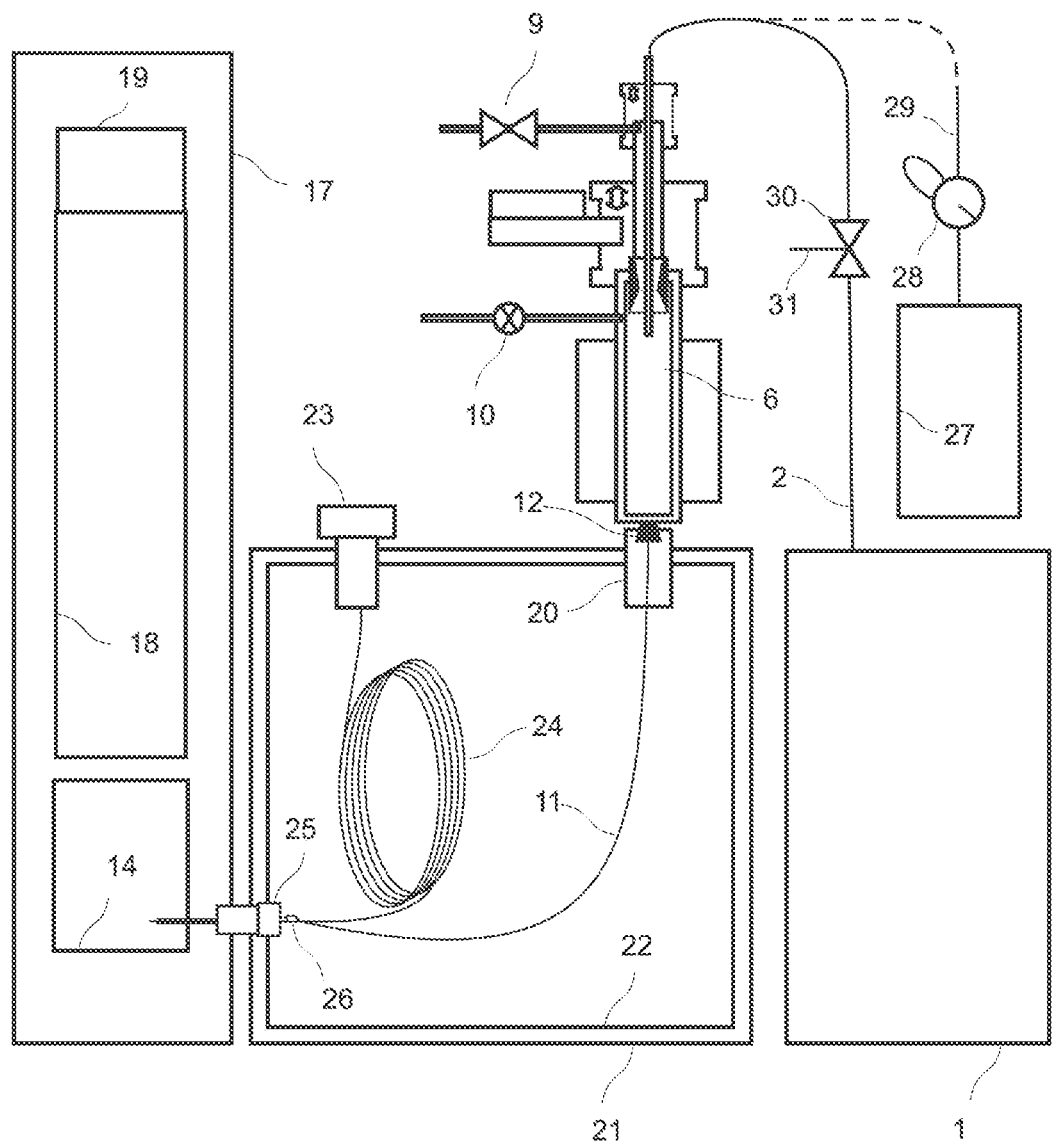
FIG. 2 is a schematic diagram illustrating the combined unified Electron Ionization GC-MS and Electron Ionization LC-MS with one mass spectrometer system according to an embodiment of the present invention.

In FIG. 2 we show a schematic diagram of a combined unified EI-LC-MS and GC-MS system with a single EI ion source and mass analyzer. The sample can be separated and elute either from the liquid chromatography (LC) component (1) (with its separation column) or a gas chromatography (GC) component (21) after its introduction to the GC via a GC injector (23) and its separation by a GC column (24). The LC liquid flow output (after sample separation by LC column) is transferred via a tube (2) into a spray formation and vaporization unit (6) whose components are shown in FIG. 1 and described above. However, this pneumatic spray formation and vaporization unit is now mounted on top of the GC (21), preferably at its GC detector slot (not shown). Thus, the output of the spray formation and vaporization unit is split via a split valve (10) mostly out into the ambient environment and a small portion of it into a heated capillary flow restrictor (11) that is sealed by ferrule (12). The flow restriction capillary enters the GC oven (22) at the entrance (20) (typically GC detector entrance) where it is heated and is maintained at high temperatures during LC-MS analysis and temperature program conditions during typical GC-MS analysis. We note that while the interface can be mounted in place of a GC injector as a modified GC injector, the GC detector slots are usually empty and available in GC-MS systems while access to GC injectors can be obstructed by the GC autosampler. For this reason, the GC detector slot is usually preferred. Both the flow restriction capillary (11) and the GC separation column (24) are connected to the MS transfer line (25) that is sealed to the MS vacuum chamber via a dual hole seal (26) that serves for the sealing of both flow restriction capillary (11) and GC column (24). Both the flow restriction capillary (11) and GC capillary column (24) end at the EI ion source (14) and the EI formed ions are mass analyzed by a mass analyzer (18) and detected by an ion detector (19), both of which are placed in a vacuum chamber (17). This way we have a unified EI-LC-MS and GC-MS system with a single mass spectrometer mass analyzer that is characterized by automated mode of operation change without any hardware change. When the GC-MS is operated, the GC oven is typically under temperature program conditions while the LC liquid flow into the spray formation and vaporization chamber is zero or very low or it is directed outside via a valve (30) into liquid split line (31) and the split valve (10) of the spray formation and vaporization chamber is fully open so that its pressure is close to (only slightly above) ambient atmospheric pressure and thus the added helium flow rate into the ion source is only about 0.3 ml/min that practically does not affect the GC-MS operational performance. When the EI-LC-MS is operated the GC injector pressure is reduced to about one atmosphere so that the added flow rate via its capillary column is similarly low at about 0.3 ml/min of pure helium that practically does not affect the EI-LC-MS operation while the GC oven is maintained at about 250-350° C. to serve as a portion of the heated flow restriction capillary transfer line. All these mode-related changes can be applied under software control.

In addition to LC-MS and GC-MS the MS system according to the present invention can further include access to a syringe pump (27) that serves for flow injection analysis via a flow injection valve (28) and a separate liquid flow tube (29). This flow injection capability can serve in both GC-MS and LC-MS modes for real time analysis as with an MS probe. When the flow injection mode is being used the LC pump can be either be stopped or sealed by valve (30) or preferably the LC solvent can be simply directed into the waist via tubing (31) at the three way valve (30). We note that the use of such a 3-way valve (30) is also preferred in the change from EI-LC-MS into GC-MS as this way the LC solvent flow rate into the EI ion source can be computer controlled to become zero while the actual LC flow rate can be retained.

It should be mentioned that:

A. Typical flow restriction capillary length is now 60 cm and thus it can use capillary I.D. of 0.12 mm for optimal gas and vaporized liquid flow rates into the EI ion source.

B. The optimal mounting of the spray formation and vaporization chamber is at a GC detector slot that is usually available in GC-MS systems that typically includes a small hole into the GC oven. A GC injector slot can also be used but in some cases it can interfere with the auto-sampler operation. Obviously it can also be placed at several other places on the top or side of the GC.

C. While having two capillaries entering into the in-vacuum EI ion source is the simplest solution for the unified GC-MS and EI-LC-MS in a single integrated system, an alternative arrangement can include the connection of these two capillaries (GC column and EI-LC-MS flow restriction capillary) into an inert (passivated) T junction while connecting this T junction into the heated transfer line as usual with a one short flow restriction capillary.

Figure 3:
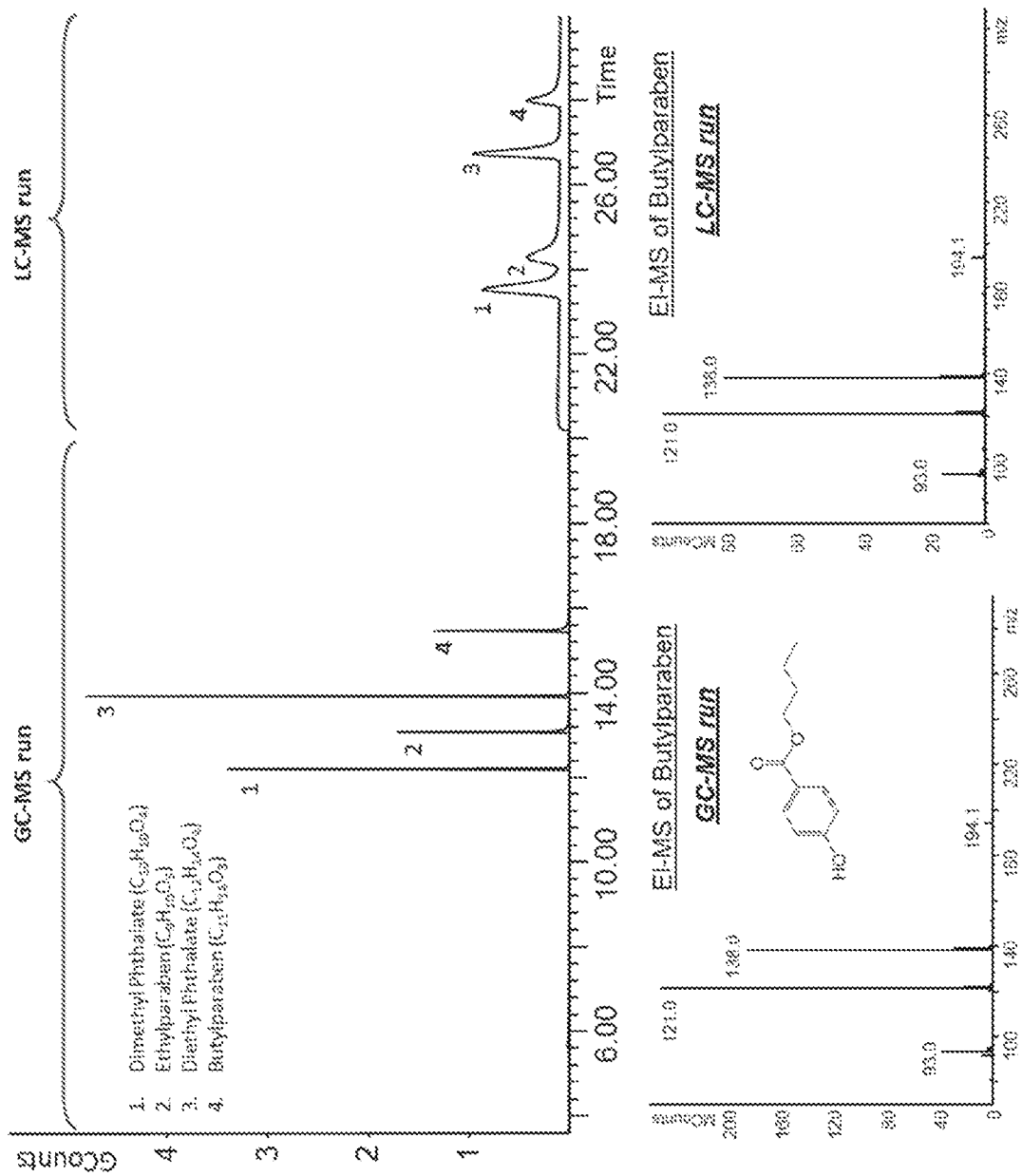
FIG. 3 shows GC-MS and LC-MS analyses in a single analysis run thereby demonstrating that the unified GC-MS and EI-LC-MS system can operate with software based mode changing and generate both analyses in a single file without any hardware movement.

In FIG. 3 we show the operation of the unified GC-MS and LC-MS system according to the present invention via the demonstration of both GC-MS and EI-LC-MS analyses in a single analysis run thereby demonstrating for the first time that the unified GC-MS and LC-MS system can operate with software-based mode changing (GC-MS or EI-LC-MS) and generate both analyses even in a single file without any hardware movement. The GC-MS sample was a mixture of 125 ppm each Dimethyl Phthalate, Ethylparaben, Diethyl Phthalate and Butylparaben (according to their order of elution times) in methanol solvent. The analysis started in the GC-MS mode with GC oven temperature of 50° C. with 1 µL injection with split factor of 50 so that 2.5 nanograms of each compound were introduced on-column. The helium GC column flow rate was 1 ml/min for 20 min then reduced to 0.4 ml/min via method based injector head pressure reduction. The GC oven temperature program started at 50° C. and it was programmed up to 250° C. at 10° C./min and held at 250° C. for 12 min so that the GC oven served at this temperature as a portion of the heated transfer line for the following LC-MS analysis.

At 20 min the LC valve that diverted the LC liquid output (valve 30 in FIG. 2) was set (opened) to let the liquid flow into the spray formation and vaporization chamber and the full 50 µL/min LC output flow rate was directed into the spray formation and vaporization chamber. The solvent inevitably includes some impurities hence baseline increase is observed when vaporized solvent enters the EI ion source. The LC-MS sample was the same parabens and phthalates mixture as analyzed by the GC-MS but in 50% methanol/water solvent and in this case 5 µL were injected without any split before the column. The LC initial mobile phase was 50% water and 50% methanol with step function methanol increase to 75% at 1 min and the column was 1 mm I.D. 50 mm long with 3µ C18 particles. As demonstrated in FIG. 3, we obtained both GC-MS and LC-MS separations and analyses in a single file thereby demonstrating that no hardware was changed in the transition from GC-MS analysis to EI-LC-MS analysis while using the same mass spectrometer mass analyzer and standard EI ion source (Agilent model 5975C MSD, Agilent Santa Clara Calif. USA). Any valve position change that was employed during analysis can be automated. It is to be noted that the EI mass spectra that were obtained and shown for butylparaben are similar in both GC-MS and LC-MS and have high NIST library matching factors of 947 in GC-MS and 919 in EI-LC-MS.

Accordingly, we have described and demonstrated an EI-LC-MS and GC-MS in a unified system with automated mode of operation change without hardware change. Clearly this is a highly desirable unified chromatography mass spectrometry system that saves cost, bench-space, operating personal and brings unique value in the form of electron ionization LC-MS mass spectral information.

In FIGS. 2 and 3 we described and demonstrated the operation of the novel combined unified EI-LC-MS and GC-MS with one mass spectrometer system that is characterized by automated GC-MS or EI-LC-MS mode of operation change without any change in hardware. The mass spectrometer was operated with a standard in-vacuum EI ion source with and thus the heated flow restriction capillary led the vaporized sample compounds and solvent and nebulizing gas directly into the ion source.

It will be appreciated by those skilled in the art that liquid chromatography and gas chromatography are carried out under different conditions of pressure, flow rate and other operating parameters for which typical preferred values are described above. Dedicated mass spectrometer systems are commonly operated under control of computer programs that allow the relevant operating parameters to be set using a graphical user interface. The present invention likewise contemplates use of a suitably modified user interface that allows for user selection of either gas chromatography mass spectrometry (GC-MS) or electron ionization liquid chromatography mass spectrometry (EI-LC-MS) analyses. Such an interface may present respective command buttons, option buttons or other icons for the two modes allowing the required mode to be selected using a mouse click, although obviously other approaches may be employed.

Upon selection of the desired mode of operation, software will then set the operating parameters best suited for the selected mode and, in the case of the interface shown in FIG. 2, may automatically operate the valve 30 in which case the valve 30 is an electrically controlled device that is opened when the liquid chromatography component is selected so as allow the liquid solvent output flow to enter into the spray formation and vaporization chamber. When the gas chromatography component is selected, the valve 30 is shut thereby blocking the flow of liquid solvent from the liquid chromatography component into the spray formation and vaporization chamber and is typically diverted to the ambient environment via the tube 31. Alternatively, the flow rate may simply be reduced to such a low value that there is negligible flow.

Although not shown in FIG. 2, the liquid chromatography component has an auto-sampler for allowing automatic injection of the sample. Operation of the auto-samplers can also be software controlled according to which mode of operation is selected, such that clicking on or otherwise selecting the required mode of operation, automatically selects the correct auto-sampler, controls the valves, the flow rates and sets all the operating parameters according to the selected mode.

The methods of electron ionization LC-MS and unified GC-MS and EI-LC-MS in one MS system as described above are highly innovative and surprising for the following reasons:

1. No one combined LC-MS with a standard EI ion source with closed metallic ion generation volume and electric field gradient with above ambient pressure sample vaporization chamber despite continuous research and many publications in this area by a few groups in the last two decades;
2. No one combined LC-MS with standard EI ion source with closed metallic ion generation volume and electric field gradient with above ambient pressure sample vaporization chamber equipped with a split valve that directs most of the LC solvent and vaporized sample out to the ambient environment, despite continuous research and many publications in this area by a few groups in the last two decades;
3. EI-LC-MS enables the most accurate identification method for LC-MS including via EI libraries that provide identifications with names and structures at the isomer structural level;
4. The integration of GC-MS and LC-MS in a single MS system is a long felt need for everyone in the art. Saving cost, bench space, system operator and system maintenance are all very well appreciated benefits. Thus, the unavailability of such a unified system testifies to the novelty of the invention according to the present patent application;
5. Sample vaporization from its spray of solvent droplets at above ambient pressure requires a heated adjustable split valve that prima facie is prone to clogging, particularly when most of the sample and solvent exit via this valve and thus deters from such use.
6. The required very high split ratio of typically over 100 between the sample and solvent that is directed into the ion source versus the vast majority that is directed outside the system could be assumed to be unstable if the flow restriction transfer line (or split valve) would be partially clogged. This was one of our major challenges to ensure a stable signal with the use of a capillary flow restrictor with the required tiny internal diameter such as of 100 µm;
7. Pneumatic spray (unlike thermally assisted spray (Thermospray)) requires the addition of gas and with in-vacuum EI ion source nitrogen cannot be used due to its known generation of excessive intra-ion-source space charge. Consequently, the use of helium is mandatory. However, typical pneumatic spray as used in ESI or APCI or APPI based LC-MS systems requires several liters per minute gas flow rates which for the expensive and scarce helium is totally unacceptable. Thus, in order to mitigate this major obstacle we developed a miniaturized pneumatic spray source that requires only 150 ml/min helium flow rate as described in this patent application. Accordingly, the design further required careful positioning of the liquid delivery capillary at the spray nozzle with its accurate adjustment mechanism (element 3 in FIG. 1);
8. The ability to tune and optimize the split ratio and thus the amount of solvent vapor that enters the EI ion source to about 0.2-0.3 µL/min is surprising and was initially unexpected. It brings the important benefits of elimination of intra-ion-source chemical ionization that deteriorate EI library based identification and provide better sensitivity as well as much longer ion source filament life time;
9. The ability to work with EI ion source with its standard filament being turned on continuously while having steady solvent flow into it is surprising and against common experience and the GC-MS instruments vendor's recommendations to turn off the filament operation during solvent elution times (named solvent delay).
10. The vaporization of the full LC liquid flow inside the spray formation and vaporization chamber can generate fear from its quick contamination particularly with buffers. However, we found that the large bore (4 mm I.D.) liners that we use have long lifetime and unlike the metallic EI ion source surface it can tolerate significantly more contamination since liner contamination buildup (unlike ion source contamination) does not affect any intra-ion-source electrical fields which is an unexpected benefit;
11. We found that the spray head location at the spray formation and vaporization chamber is unexpectedly very important and we needed to develop a precise mechanism for its control (element 5 in FIG. 1). This is since in order to have a stable spray we need the solvent to be at temperatures well below its boiling point while for tailing-free sample vaporization we need the spray droplets to scatter from a hot and preferably inert surface and all this with low pneumatic spray helium flow rate. Thus, we developed the maximum axial temperature gradient concept that was used with inert glass liners that are with low temperature conductivity;
12. We bring two capillaries directly into the in-vacuum EI ion source in the unified GC-MS and EI-LC-MS in one system which is not being used even in the world of GC-MS with EI ion source. It can generate the fear of increases total intra ion source pressure hence reduced performance of the ion source;

REFERENCES

[1] A. Cappiello, M. Balogh, G. Famiglini, A. Filippo Mangani, and P. Palma, "An Efficient Liquid Chromatography-Mass Spectrometry Interface for the Generation of Electron Ionization Spectra," Anal. Chem. 72, 3841-3846, (2000).
[2] A. Cappiello, G. Famiglini, E. Pierini, A. P. Palma, and H. Trufelli, "Advanced Liquid Chromatography-Mass Spectrometry Interface Based on Electron Ionization," Anal. Chem. 79, 5364-5372, (2007).
[3] V. Termopoli, G. Famiglini, P. Palma, M. Piergiovanni, and A. Cappiello, "Atmospheric Pressure Vaporization Mechanism for Coupling a Liquid Phase with Electron Ionization Mass Spectrometry," Anal. Chem. 89, 2049-2056, (2017).
[4] B. Seemann, T. Alon, S. Tsizin, A. B. Fialkov and A. Amirav "Electron Ionization LC-MS with Supersonic Molecular Beams—The New Concept Benefits and Applications" J. Mass. Spectrom. 50, 1252-1263 (2015).
[5] A. Amirav, "Capillary separated vaporization chamber and nozzle device and method" U.S. Pat. No. 8,604,424 Dec. 10, 2013.

The invention claimed is:
1. A method for electron ionization liquid chromatography mass spectrometry (EI-LC-MS) analysis, the method including:
 a) directing a liquid chromatograph output liquid solvent flow together with spray formation gas into a spray formation and vaporization chamber for forming spray droplets from said liquid chromatograph output liquid solvent flow and vaporizing said droplets to form vaporized sample compounds in said solvent at a pressure equal to or greater than ambient pressure;
 b) splitting the vaporized sample compounds, solvent and spray formation gas into a minor portion and a major portion;
 c) transferring the minor portion into a heated flow restriction capillary that directly connects said spray formation and vaporization chamber and a non-fly-through electron ionization ion source of a mass spectrometer which is located inside a vacuum chamber;
 d) releasing the major portion of the vaporized sample, solvent and spray gas mixture to atmosphere so that it does not enter said flow restriction capillary and therefore does not reach the non-fly-through electron ionization ion source.
2. A method for electron ionization gas chromatography mass spectrometry (GC-MS) and electron ionization liquid chromatography mass spectrometry (EI-LC-MS) analysis in a unified mass spectrometer system having an electron ionization (EI) ion source and a mass analyzer, the method including:
 a) performing the EI-LC-MS and GC-MS analyses having a common electron ionization (EI) ion source and mass analyzer;
 b) changing between GC-MS and EI-LC-MS modes of operation without manual hardware modification;
 c) directing a liquid chromatograph output liquid solvent flow together with spray formation gas into a spray formation and vaporization chamber for forming spray droplets from said liquid chromatograph output liquid solvent flow and vaporizing said droplets to form vaporized sample compounds in said solvent at a pressure equal to or greater than ambient pressure;
 d) splitting the vaporized sample compounds, solvent and spray formation gas into a minor portion and a major portion;
 e) transferring the minor portion into a heated flow restriction capillary that directly connects said spray formation and vaporization chamber and an electron ionization ion source of a mass spectrometer which is located inside a vacuum chamber;

f) releasing the major portion of the vaporized sample, solvent and spray gas mixture to atmosphere so that it does not enter said flow restriction capillary and therefore does not reach the electron ionization ion source.

3. The method according to claim 2 wherein said heated flow restriction capillary directs the vaporized sample compounds, solvent and spray formation gas into an ionization area of the electron ionization ion source.

4. The method according to claim 1, including maintaining a temperature gradient zone higher than 60° C./cm at an entrance to the said spray formation and vaporization chamber.

5. The method according to claim 1, including forming a pneumatic spray using a spray head having a liquid delivery capillary and a pneumatic spray generation orifice, and adjustably positioning the liquid delivery capillary within a range of 0.3 mm upstream of said orifice up to 1 mm downstream of said orifice.

6. The method according to claim 1, including forming a pneumatic spray using a suitable spray head and positioning the spray head at a selected temperature zone in the spray formation and vaporization chamber.

7. The method according to claim 1, wherein said heated flow restriction capillary is dimensioned to reduce vaporized liquid flow rate into said electron ionization ion source to below 1 µL/min (as liquid) at ambient capillary flow restriction head pressure.

8. The method according to claim 1, wherein the minor portion is at least 30 times smaller than the major portion.

9. The method according to claim 1, wherein said LC liquid flow rate into said spray formation and vaporization chamber is greater than 20 µl/min.

10. The method according to claim 1, including servicing said spray formation and vaporization chamber without venting the mass spectrometer system.

11. The method according to claim 2, including maintaining a temperature gradient zone higher than 60° C./cm at an entrance to the said spray formation and vaporization chamber.

12. The method according to claim 2, including forming a pneumatic spray using a spray head having a liquid delivery capillary and a pneumatic spray generation orifice, and adjustably positioning the liquid delivery capillary within a range of 0.3 mm upstream of said orifice up to 1 mm downstream of said orifice.

13. The method according to claim 2, including forming a pneumatic spray using a suitable spray head and positioning the spray head at a selected temperature zone in the spray formation and vaporization chamber.

14. The method according to claim 2, wherein said heated flow restriction capillary is dimensioned to reduce vaporized liquid flow rate into said electron ionization ion source to below 1 µL/min (as liquid) at ambient capillary flow restriction head pressure.

15. The method according to claim 2, wherein the minor portion is at least 30 times smaller than the major portion.

16. The method according to claim 2, wherein said LC liquid flow rate into said spray formation and vaporization chamber is greater than 20 µl/min.

17. An interface for an electron ionization liquid chromatography mass spectrometry (EI-LC-MS) system having a liquid chromatography component, an electron ionization component and a mass analyzer component for allowing electron ionization liquid chromatography mass spectrometry to be carried out, said interface including:

a spray formation and vaporization chamber adapted for coupling to an output of the liquid chromatography component for receiving therefrom liquid solution output flow together with spray formation gas for forming spray droplets and for vaporizing said droplets to form vaporized sample compounds at pressure equal or greater than ambient pressure;

a split valve for splitting the vaporized sample compounds, solvent and spray formation gas into a minor portion and a major portion; and a heated flow restriction capillary adapted for direct connection between said spray formation and vaporization chamber and a non-fly-through electron ionization ion source for directing the minor portion into the non-fly-through electron ionization ion source located at a vacuum chamber;

whereby the major portion of the vaporized sample, solvent and spray gas mixture is released to atmosphere via the split valve so that it does not enter the flow restriction capillary and therefore does not reach the electron ionization ion source.

18. A unified dual-mode mass spectrometer system for selectively performing gas chromatography mass spectrometry (GC-MS) or electron ionization liquid chromatography mass spectrometry (EI-LC-MS) analyses, said unified mass spectrometer system having (i) a gas chromatography component containing an oven and a separation column and (ii) a liquid chromatography component, said gas chromatography component and liquid chromatography component being commonly coupled to a vacuum chamber containing an electron ionization (EI) ion source and a mass analyzer and said unified dual-mode mass spectrometer system further comprising:

a spray formation and vaporization chamber adapted for coupling to an output of the liquid chromatography component for receiving therefrom liquid solution output flow together with spray formation gas for forming spray droplets and for vaporizing said droplets to form vaporized sample compounds at pressure equal or greater than ambient pressure;

a split valve for splitting the vaporized sample compounds, solvent and spray formation gas into a minor portion and a major portion; and a heated flow restriction capillary adapted for direct connection between said spray formation and vaporization chamber and the electron ionization ion source for directing the minor portion into the electron ionization ion source located inside said vacuum chamber; and said gas chromatography component having a heated GC column transfer line for the connection of gas chromatography component into electron ionization ion source for enabling GC-MS analysis; and said heated GC column transfer line further includes a flow restriction capillary adapted for direct connection between said spray formation and vaporization chamber and the electron ionization ion source, an automatic mode-change selector for changing a mode of operation without any hardware change between EI-LC-MS and GC-MS while allowing use of said electron ionization (EI) ion source and mass spectrometer mass analyzer in both modes;

the major portion of the vaporized sample, solvent and spray gas mixture being released to atmosphere so that it does not enter the flow restriction capillary and therefore does not reach the electron ionization ion source.

19. The mass spectrometer system according to claim 17, wherein said heated flow restriction capillary directs the vaporized sample compounds, solvent and spray formation gas into an ionization area of the electron ionization ion source.

20. The mass spectrometer system according to claim 17, wherein the spray formation and vaporization chamber includes a spray head having a liquid delivery capillary and a pneumatic spray generation orifice, and an adjustably positioning device for positioning the liquid delivery capillary within a range of 0.3 mm upstream of said orifice up to 1 mm downstream of said orifice.

21. The mass spectrometer system according to claim 17, wherein the spray formation and vaporization chamber includes a spray head having a positioning device for positioning the spray head at a selected temperature zone in the spray formation and vaporization chamber.

22. The mass spectrometer system according to claim 17, wherein said heated flow restriction capillary is dimensioned to reduce vaporized liquid flow rate into said electron ionization ion source to be below 1 μL/min (as liquid) at ambient capillary flow restriction means head pressure.

23. The mass spectrometer system according to claim 17, wherein said split valve and the heated flow restriction capillary provide a split ratio greater than 30 between the minor portion and the major portion.

24. The mass spectrometer system according to claim 17, wherein the flow restriction capillary and the separation column are connected to a mass spectrometer transfer line and said interface is configured for mounting on the ambient pressure side of the mass spectrometer transfer line to the electron ionization ion source.

25. The mass spectrometer system according to claim 18, wherein said interface is configured for mounting on top of the gas chromatograph oven.

26. The mass spectrometer system according to claim 18, wherein said interface is placed on a GC detector slot on top of the gas chromatograph oven.

27. The mass spectrometer system according to claim 17, wherein said LC liquid flow rate into said spray formation and vaporization chamber is above 20 μl/min.

28. The mass spectrometer system according to claim 18, wherein the liquid chromatograph component is interfaced with the electron ionization ion source component via two capillaries that are placed inside said gas chromatograph oven and are further transferred to the mass spectrometer ion source via a heated transfer line.

29. The mass spectrometer system according to claim 18, wherein said heated flow restriction capillary directs the vaporized sample compounds, solvent and spray formation gas into an ionization area of the electron ionization ion source.

30. The mass spectrometer system according to claim 18, wherein the spray formation and vaporization chamber includes a spray head having a liquid delivery capillary and a pneumatic spray generation orifice, and an adjustably positioning device for positioning the liquid delivery capillary within a range of 0.3 mm upstream of said orifice up to 1 mm downstream of said orifice.

31. The mass spectrometer system according to claim 18, wherein the spray formation and vaporization chamber includes a spray head having a positioning device for positioning the spray head at a selected temperature zone in the spray formation and vaporization chamber.

32. The mass spectrometer system according to claim 18, wherein said heated flow restriction capillary is dimensioned to reduce vaporized liquid flow rate into said electron ionization ion source to be below 1 μL/min (as liquid) at ambient capillary flow restriction means head pressure.

33. The mass spectrometer system according to claim 18, wherein said split valve and the heated flow restriction capillary provide a split ratio greater than 30 between the minor portion and the major portion.

34. The mass spectrometer system according to claim 18, wherein said LC liquid flow rate into said spray formation and vaporization chamber is above 20 μl/min.

* * * * *